(12) United States Patent
Varmette et al.

(10) Patent No.: US 7,468,520 B1
(45) Date of Patent: Dec. 23, 2008

(54) SYSTEM AND METHOD FOR LIGHT INDUCED FLUORESCENCE DETECTION

(75) Inventors: Peter George Varmette, Huntsville, AL (US); Michael James Lowe, Scottsboro, AL (US); Michael Francis Baran, Madison, AL (US)

(73) Assignee: Science Applications International Corporation, San Diego, CA (US)

( * ) Notice: Subject to any disclaimer, the term of this patent is extended or adjusted under 35 U.S.C. 154(b) by 0 days.

(21) Appl. No.: 12/078,182

(22) Filed: Mar. 27, 2008

Related U.S. Application Data (63) Continuation of application No. 11/491,093, filed on Jul. 24, 2006, now Pat. No. 7,381,972.

(51) Int. Cl.
*G01N 21/64* (2006.01)

(52) U.S. Cl. .................. 250/458.1; 250/459.1
(58) Field of Classification Search .............. 250/458.1, 250/459.1
See application file for complete search history.

(56) References Cited

U.S. PATENT DOCUMENTS

| | | | | |
|---|---|---|---|---|
| 3,825,762 | A | * | 7/1974 | White ..................... 250/458.1 |
| 4,833,332 | A | * | 5/1989 | Robertson et al. ......... 250/458.1 |
| 4,897,551 | A | | 1/1990 | Gersh et al. ............. 250/461.1 |
| 4,977,325 | A | | 12/1990 | Bowen et al. ............ 250/461.2 |
| 4,983,846 | A | | 1/1991 | Rios et al. ............... 250/458.1 |
| 5,157,261 | A | | 10/1992 | Grey et al. .............. 250/458.1 |
| 5,281,826 | A | | 1/1994 | Ivancic et al. ........... 250/461.1 |
| 5,306,642 | A | | 4/1994 | Reagen et al. ............. 436/106 |
| 5,424,959 | A | | 6/1995 | Reyes et al. .................... 702/28 |
| 5,448,082 | A | | 9/1995 | Kim ............................ 257/82 |
| 5,512,758 | A | | 4/1996 | Kobayashi et al. ....... 250/461.1 |
| 5,569,366 | A | | 10/1996 | Chen et al. .................. 204/452 |
| 5,617,205 | A | | 4/1997 | Dou et al. .................... 356/301 |
| 5,760,898 | A | | 6/1998 | Haley et al. ................ 356/318 |
| 5,912,466 | A | | 6/1999 | Funsten et al. ............. 250/372 |

(Continued)

FOREIGN PATENT DOCUMENTS

EP  0806652 A2  11/1997

(Continued)

OTHER PUBLICATIONS

Eskow, Cary, "Designing Illumination Systems with High-Brightness LEDs," Light Matters, LightSpeed, 1 p., www.avnet.com, Dec. 2006.

(Continued)

*Primary Examiner*—David P Porta
*Assistant Examiner*—Mark R Gaworecki
(74) *Attorney, Agent, or Firm*—King & Spalding LLP (57) ABSTRACT

A device for determining the presence or absence of at least one substance is described. The device includes an illumination component including at least one light emitting diode in the forward bias mode acting as an emitter and configured to illuminate a target with a first waveband; and a detection component including at least one light emitting diode in the reverse bias mode acting as a detector and configured to detect a second waveband emitted by the target in response to the first waveband if the target contains a threshold amount of the at least one substance, wherein, the illumination component and the detection component are included in a single head unit module.

57 Claims, 9 Drawing Sheets

U.S. PATENT DOCUMENTS

| | | | |
|---|---|---|---|
| 5,937,026 A | 8/1999 | Satch | 378/44 |
| 6,043,506 A | 3/2000 | Heffelfinger et al. | 250/584 |
| 6,178,227 B1 | 1/2001 | Sato | 378/117 |
| 6,263,291 B1 | 7/2001 | Shakespeare et al. | 702/85 |
| 6,266,390 B1 | 7/2001 | Sommer, Jr. et al. | 378/45 |
| 6,410,940 B1 | 6/2002 | Jiang et al. | 257/82 |
| 6,459,767 B1 | 10/2002 | Boyer | 378/121 |
| 6,490,030 B1 | 12/2002 | Gill et al. | 356/71 |
| 6,501,825 B2 | 12/2002 | Kaiser et al. | 378/45 |
| 6,505,059 B1 | 1/2003 | Kollias et al. | 600/316 |
| 6,519,315 B2 | 2/2003 | Sommer, Jr. et al. | 378/45 |
| 6,771,369 B2 | 8/2004 | Rzasa et al. | 356/326 |
| 6,794,645 B2 | 9/2004 | Kanik et al. | 250/288 |
| 6,797,944 B2 | 9/2004 | Nguyen et al. | 250/286 |
| 6,868,344 B1 | 3/2005 | Nelson | 702/31 |
| 6,903,817 B2 | 6/2005 | Sarger et al. | 356/318 |
| 6,936,827 B1 | 8/2005 | Mohler | 250/458.1 |
| 6,984,524 B2 | 1/2006 | Nguyen et al. | 436/107 |
| 7,006,214 B2 | 2/2006 | Rzasa et al. | 356/300 |
| 7,092,485 B2 | 8/2006 | Kravis | 378/57 |
| 7,106,826 B2 | 9/2006 | Poteet et al. | 378/45 |
| 7,154,102 B2 | 12/2006 | Poteet et al. | 250/372 |
| 2002/0022766 A1 | 2/2002 | Adachi | 600/160 |
| 2002/0158211 A1 | 10/2002 | Gillispie | 250/458.1 |
| 2002/0197728 A1 | 12/2002 | Kaufman et al. | 436/164 |
| 2003/0020618 A1 | 1/2003 | Hemmer et al. | 340/632 |
| 2003/0128804 A1 | 7/2003 | Poteet et al. | 378/44 |
| 2003/0160182 A1* | 8/2003 | Petrich et al. | 250/458.1 |
| 2003/0160231 A1 | 8/2003 | Cole et al. | 257/22 |
| 2004/0007665 A1 | 1/2004 | DiFoggio et al. | 250/269.1 |
| 2004/0051867 A1 | 3/2004 | Mordechai et al. | 356/318 |
| 2004/0063214 A1 | 4/2004 | Berlin et al. | 436/94 |
| 2004/0085535 A1 | 5/2004 | Hammer et al. | 356/330 |
| 2004/0155202 A1 | 8/2004 | Poteet et al. | 250/461.1 |
| 2005/0070025 A1 | 3/2005 | Mooradian et al. | 436/178 |
| 2005/0077476 A1 | 4/2005 | Poteet et al. | 250/461.1 |
| 2005/0134836 A1 | 6/2005 | Paldus et al. | 356/73 |
| 2005/0248758 A1 | 11/2005 | Carron et al. | 356/301 |

FOREIGN PATENT DOCUMENTS

| | | | |
|---|---|---|---|
| EP | 0806652 A3 | 4/1998 | |
| EP | 1220165 A2 | 7/2002 | |
| EP | 1220165 A3 | 3/2004 | |
| GB | 2 365 966 A | 2/2002 | |
| WO | WO 02/16917 A1 | 2/2002 | |
| WO | WO 02/097407 A1 | 12/2002 | |
| WO | WO 2005/001451 | 1/2005 | |

OTHER PUBLICATIONS

News Release, "Sensors Could Detect Traces of Chemicals on Passengers" [online], Release Date Aug. 14, 2006 [retrieved on Feb. 2, 2007], 2 pp., Retrieved from the Internet: http://www.buffalo.edu/news/fast-execute.cgi/article-page.html?article=81210009.

"New York Police Department Purchases Smiths Advanced Portable Explosives Detection Equipment" [online], Jul. 27, 2006 [retrieved on Feb. 7, 2008], 1 p., Retrieved from the Internet: http://www.smithsdetection.com/eng/1025_1090.php.

Lisaius, Som, "Tucson Company Touting "Meth Gun"" [online], Jul. 14, 2006 [retrieved on Jul. 19, 2006], 2 pp., Retrieved from the Internet: http://www.kold.com/Global/story.asp?S=5148339&nav=14RT.

"Meth Detection" [online], Keloland Television, Jun. 28, 2006 [retrieved on Feb. 7, 2008], 2 pp., Retrieved from the Internet: http://web.archive.org/web/20060707224609/http://www.keloland.com/News/NewsDetail5442.cfm?Id=0,49089.

Vandebroek, Sophie, "Building Technology Partnerships," *R&D Executive Magazine*, pp. E2-E5, Jun. 2006.

Kaminski, Ron, "Inventors Say the Darndest Things, Are You Listening?," *R&D Executive Magazine*, pp. E6-E8, Jun. 2006.

Dong, Nelson, "The New Challenges of 'Deemed Exports' to China," *R&D Executive Magazine*, pp. E9-E11, Jun. 2006.

Studt, Tim, "R&D Writing Is on the Wall," *R&D Executive Magazine*, pp. E12-E13, Jun. 2006.

Studt, Tim, "U.S. Versus European Biotech," *R&D Exectuive Magazine*, p. E14, Jun. 2006.

International Search Report for Application No. PCT/US04/005320, dated Feb. 8, 2005.

Johnson, R. Colin, "Photoluminescent Method Detects Explosives at a Distance," Oct. 18, 2004 [retrieved on Dec. 3, 2007], *EE Times*, 2 pp., Retrieved from the Internet: http://www.eetimes.com/showArticle.jhtml?articleID=50500050&printable=true.

International Search Report for Application No. PCT/US03/37292, dated Apr. 23, 2004.

White, Joel, et al., "Explosives and Landmine Detection Using an Artificial Olfactory System," *SPIE*, vol. 5415, pp. 521-532, 2004.

International Search Report for Application No. PCT/US03/00259, dated Apr. 10, 2003.

Parmeter, John E., "Trace Detection of Narcotics Using a Preconcentrator/Ion Mobility Spectrometer System, NIJ Report 602-00," *National Institute of Justice, Law Enforcement and Corrections Standards and Testing Program*, 26 pp., Apr. 2001.

Al-Dirbashi, Osama Y., et al., "Drugs of Abuse in a Non-Conventional Sample; Detection of Methamphetamine and Its Main Metabolite, Amphetamine in Abusers' Clothes by HPLC with UV and Fluorescence Detection," *Biomedical Chromatography*, vol. 15, pp. 457-463 (2001).

Parmeter, John E., et al., "Guide for the Selection of Drug Detectors for Law Enforcement Applications, NIJ Guide 601-00," *National Institute of Justice, Law Enforcement and Corrections Standards and Testing Program*, 61 pp., Aug. 2000.

Cody, John T., et al., "Fluorescence Polarization Immunoassay Detection of Amphetamine, Methamphetamine, and Illicit Amphetamine Analogues," *Journal of Analytical Toxicology*, vol. 17, pp. 26-30, Jan./Feb. 1993.

Mims, III, Forrest M., "Sun Photometer With Light-Emitting Diodes as Spectrally Selective Detectors," *Applied Optics*, vol. 31, No. 33, pp. 6965-6967, Nov. 20, 1992.

* cited by examiner

SYSTEM AND METHOD FOR LIGHT INDUCED FLUORESCENCE DETECTION

CROSS-REFERENCE TO RELATED APPLICATIONS

This application is a continuation of U.S. patent application Ser. No. 11/491,093, filed Jul. 24, 2006 now U.S. Pat. No. 7,381,972, entitled "System and Method for Light Induced Fluorescence Detection," which is incorporated by reference in its entirety.

BACKGROUND OF THE INVENTION

1. Field of the Invention

The present invention is directed generally to light induced fluorescence techniques for the detection of substances. More particularly, the invention is directed to a handheld, non-contact illumination and detection device for identifying the presence or absence of specific substances including explosives, illegal drugs, chemical/biological agents, and toxic industrial chemicals.

2. Description of the Related Art

As described in the Guide for the Selection of Drug Detectors for Law Enforcement Applications, NIJ Guide 601-00, by Parmeter et al., Contraband Detection Technologies Department Sandia National Laboratories (1999) which is incorporated herein by reference in its entirety, trace detection is a common approach to the detection of narcotics, and refers to detecting the drug by collection and analysis of microscopic amounts of the drug. These microscopic quantities can be in the form of vapor, particulate, or both.

There are two primary methods of collecting trace material for delivery to a trace chemical detector: vacuuming and swiping. Vacuuming is used to collect vapor and/or airborne particulate and is usually performed with a hand-held device similar to a Dustbuster. Air is pulled through a filter pad within this device, collecting vapor or particles of illicit drugs that are present in the air. The pad is then removed and presented to a sampling port on the trace detector for analysis. A few trace detectors are designed so that air can be sucked directly into an inlet port on the detector.

Swipe collection, which is intended to collect particulate residue deposited on surfaces uses sampling pads that are wiped ("swiped") across a surface to be analyzed. These pads are usually supplied by the manufacturer of the detector used and can be applied to any surface, including clothing and skin. Once a swipe sample has been obtained, the pad is presented to a sampling port on the detector, usually in the same way as that of a vacuum sampling pad. Swiping is often more sensitive than vacuuming because it allows more particulate matter to be collected, and with low vapor pressure materials even one microscopic particle may contain a larger mass of material than would be present in a large volume of air saturated with vapor. However, swiping may sometimes be considered too invasive for purposes of personnel screening because it requires direct contact of the sampling pad with skin or clothing.

Additionally, trained canines are also used as initial trace detectors because they detect drugs from residual vapor and particle contamination.

SUMMARY OF THE INVENTION

Summary of the Problem

As described above, techniques exist for illegal drug detection through forensic and toxicological analysis of urine, blood, hair, and sweat (extracted from clothing). These trace detection techniques require sample collection from suspected abusers and laboratory processing where substances are isolated and subsequent analysis is carried out by gas chromatography-mass spectrometry (GC-MS), high-performance liquid chromatography (HPLC), radioimmunoassay (RIA), enzyme immunoassay (EIA) or enzyme-linked immunosorbent assay (ELIA). These techniques and devices require contact with the trace, i.e., obtaining a field sample which is intrusive, and may require multiple steps before a positive (or negative) determination is made, thereby lengthening considerably the time needed to confirm the presence of a particular substance. The need for actual contact increases the chances for cross-contamination, and may require some level of detector system cleansing between sample analysis. Additionally, these systems and methods are expensive and require specialized optical systems and high maintenance precision spectrometers that require time-consuming calibration steps in order to perform the required spectral analysis.

Need

Accordingly, there is a need in the art for a simple, rugged, hand-held, non-contact system which provides for the near real-time indication of the presence of a target substance.

Summary of the Solution

Throughout this disclosure, we use the term waveband to denote an illumination signal or a detected response signal that may vary in amplitude across a range of wavelengths. A typical light emitting diode (LED) emits light in a waveband centered at a particular wavelength, with the distribution about that central wavelength defined in terms of the full-width of the distribution at half the amplitude of the emitted light. Those familiar with the art refer to this as the full-width at half-max (FWHM), and for most LEDs, this width is typically 25 nanometers. LEDs operating in the detection mode exhibit this characteristic as well in their response function. LED illumination and detection characteristics including FWHM may vary depending on, e.g., manufacturing process and/or technical advance.

In accordance with a first preferred embodiment of the present invention, a device for determining the presence or absence of at least one substance is described. The device includes an illumination component configured to illuminate a target with a first waveband, and a detection component including at least one light emitting diode configured to detect a second waveband emitted by the target in response to the first waveband if the target contains a threshold amount of at least one substance, wherein the illumination component and the detection component are included in a single head unit module.

In accordance with a second preferred embodiment of the present invention, a device for determining the presence or absence of at least one substance is described. The device includes an illumination component including at least one forward bias light emitting diode configured to illuminate a target with a first waveband; and a detection component including at least one reverse bias light emitting diode configured to detect a second waveband emitted by the target in response to the first waveband if the target contains a threshold amount of the at least one substance.

In accordance with a third preferred embodiment of the present invention, a method for determining the presence or absence of at least one substance is described. The method includes illuminating a target with a first waveband to induce a fluorescence emission from the at least one substance; and detecting the fluorescence emission using at least one light emitting diode configured to detect the fluorescence emission emitted by the target in response to the first waveband if the target contains a threshold amount of the at least one substance.

BRIEF DESCRIPTION OF THE DRAWINGS

The figures summarized below are intended to be read in combination with the detailed descriptions set forth herein and are exemplary. One skilled in the art recognizes variations to these exemplary figures which clearly fall within the scope of the invention.

DETAILED DESCRIPTION OF THE PREFERRED EMBODIMENTS OF THE INVENTION

The following detailed embodiments are intended to be exemplary and not exhaustive. Those skilled in the art recognize alternative embodiments that fall within the scope of the invention exemplified herein.

In a preferred embodiment of the present invention, a system and method for the detection of trace amounts of methamphetamine, also known as meth, crystal meth, crank, and ice among other street names, is described. The system and method implement light induced fluorescence and fluorescence detection with a system of light emitting diodes.

Figure 1A:
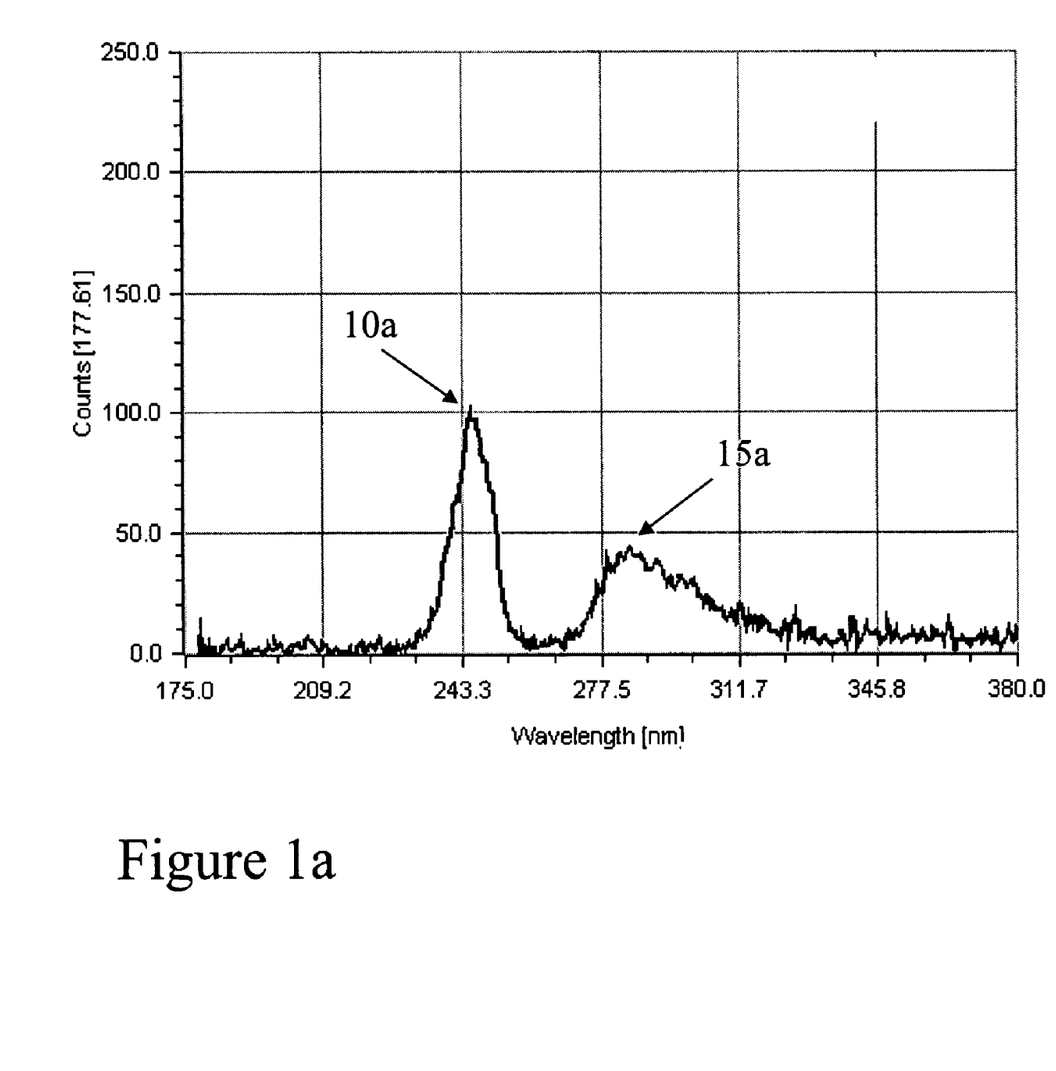
FIGS. 1a-1d illustrate methamphetamine illumination and resulting fluorescence response curves according to a preferred embodiment of the present invention.
Figure 1B:
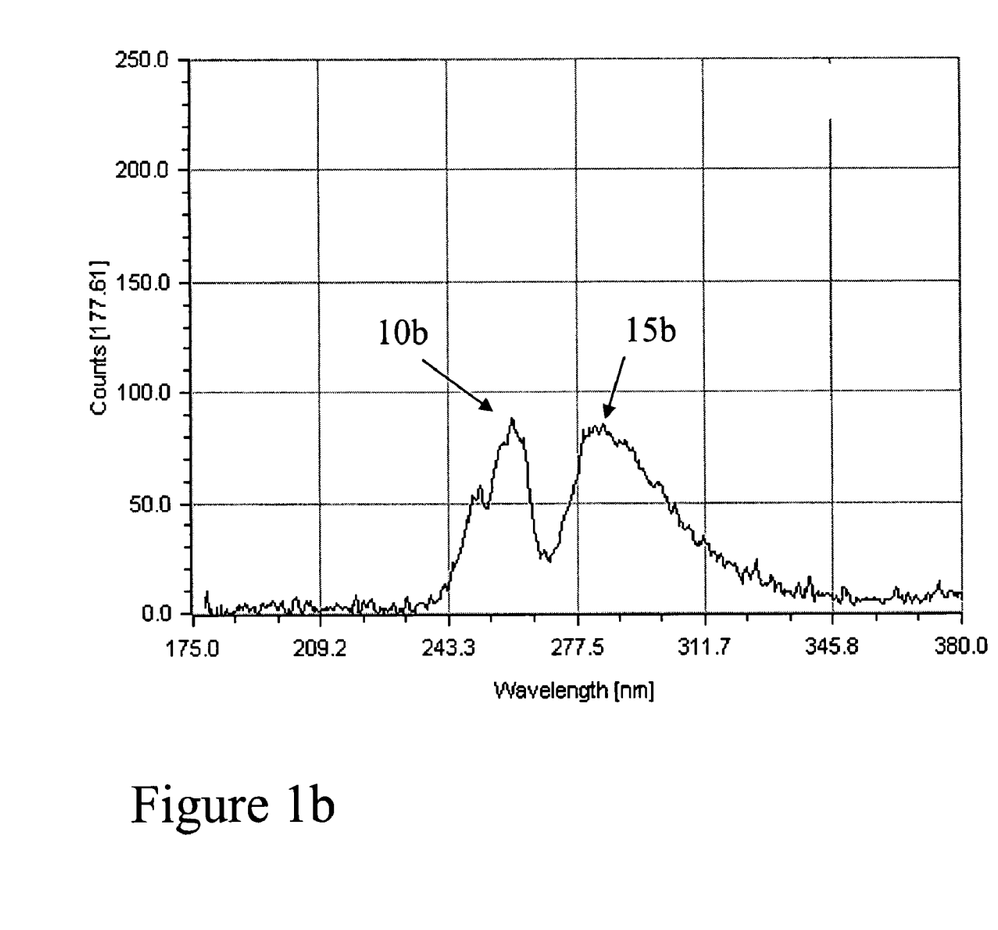
Figure 1C:
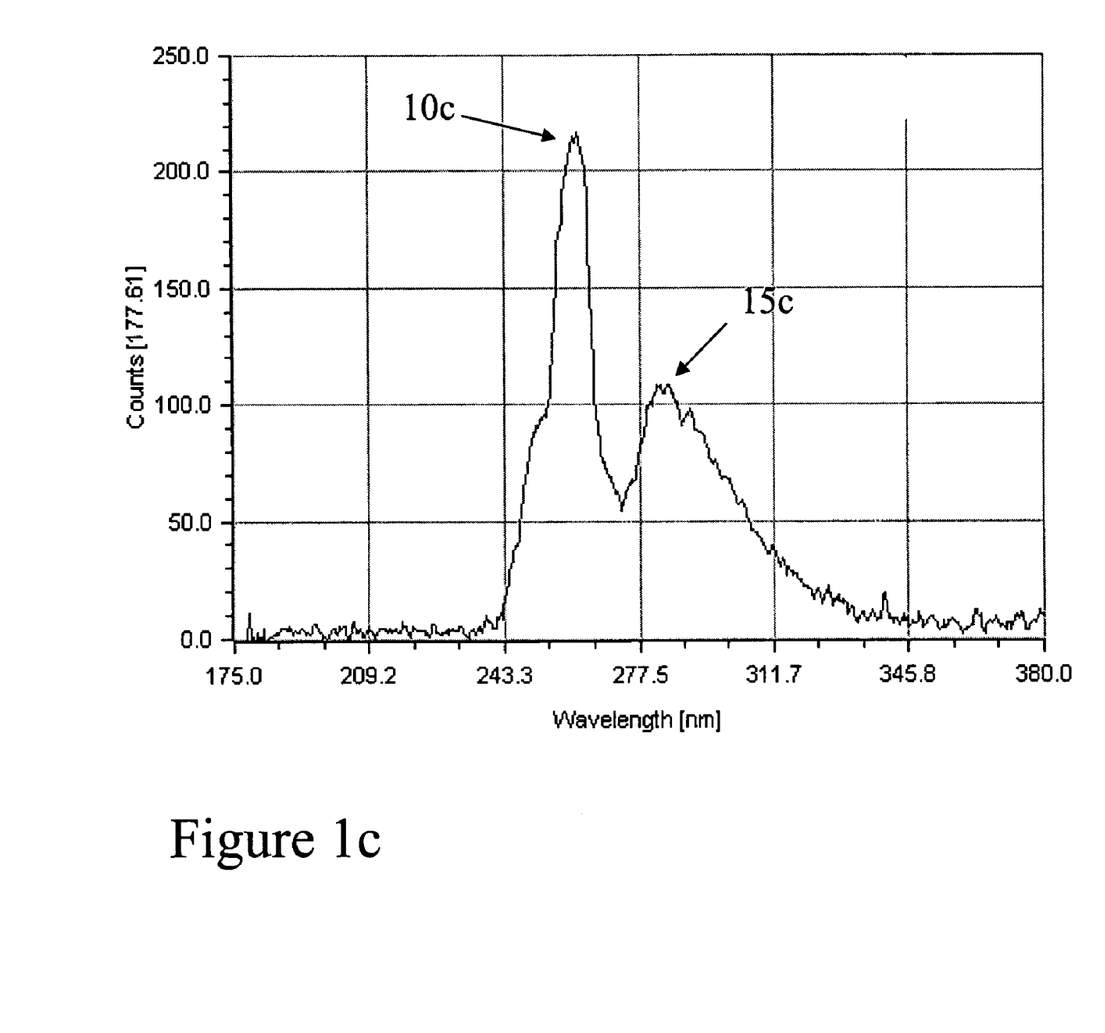
Figure 1D:
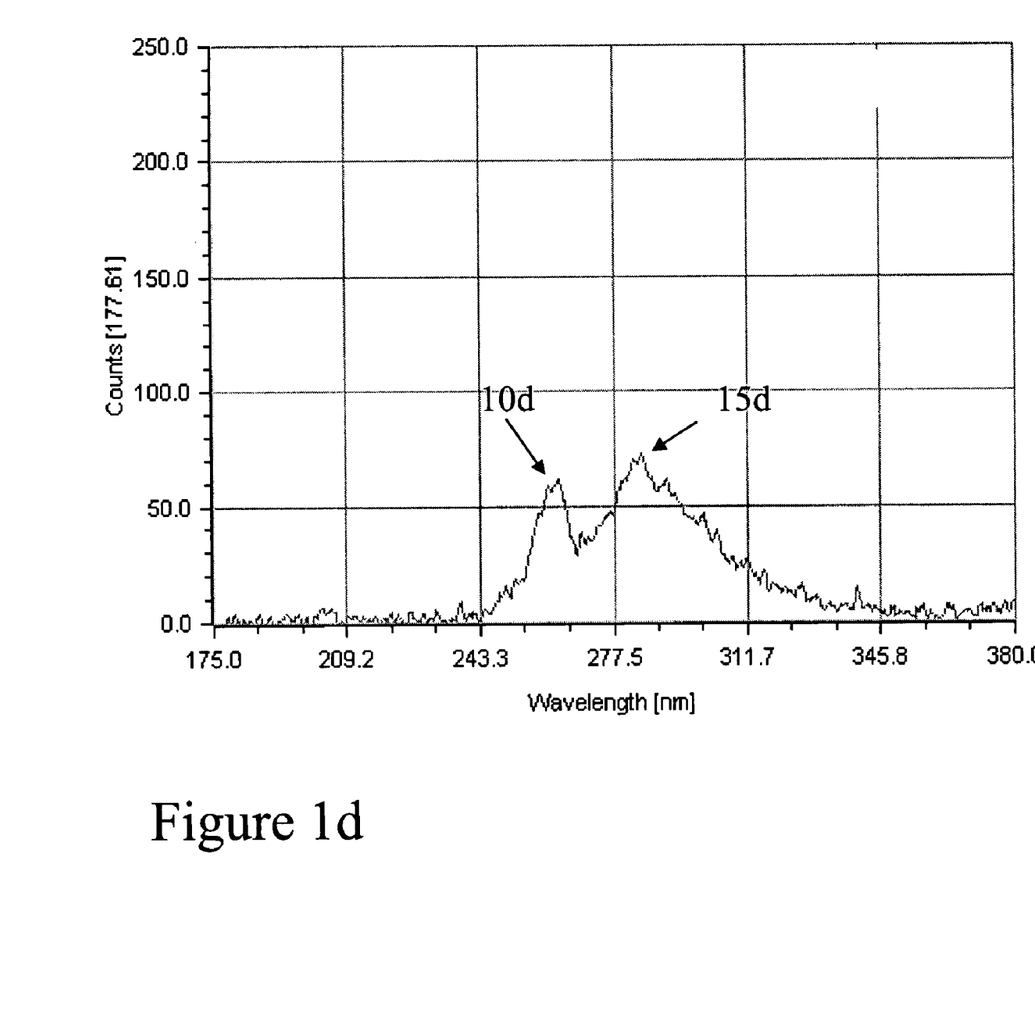

As an initial step in carrying out the method for detection of meth, it is necessary to determine the fluorescence characteristics for meth. Contrary to the published literature and expected results, meth fluorescence was detected when illuminated at the following wavebands: 233 nanometers (nm) to 259 nm centered at 245 (nm) (FIG. 1a); 240 nm to 271 nm with two peaks centered at 251 nm and 261 nm (FIG. 1b); 241 nm to 273 nm centered at 261 nm (FIG. 1c); and 245 nm to 270 nm centered at 263 nm (FIG. 1d) wherein the illumination peaks are labeled 10a-10d. While the fluorescence peak stays in the same waveband due to the molecular structure of the substance, the magnitude of the peak changes in amplitude as a function of methamphetamine concentration, illumination intensity, and center wavelength of illumination waveband. The fluorescence peaks labeled 15a-15d in FIGS. 1a-1d respectively, all start at approximately 266 nm, end at 335 nm, and are centered at 284 nm. The preferred illumination waveband for meth is centered around 261 nm, and the resulting fluorescence waveband begins at 266 nm, ends at 335 nm and is centered at 284 nm. The preferred operational range for the invention to perform illumination and detection of a substance will be from approximately 4-24 inches.

Figure 2:
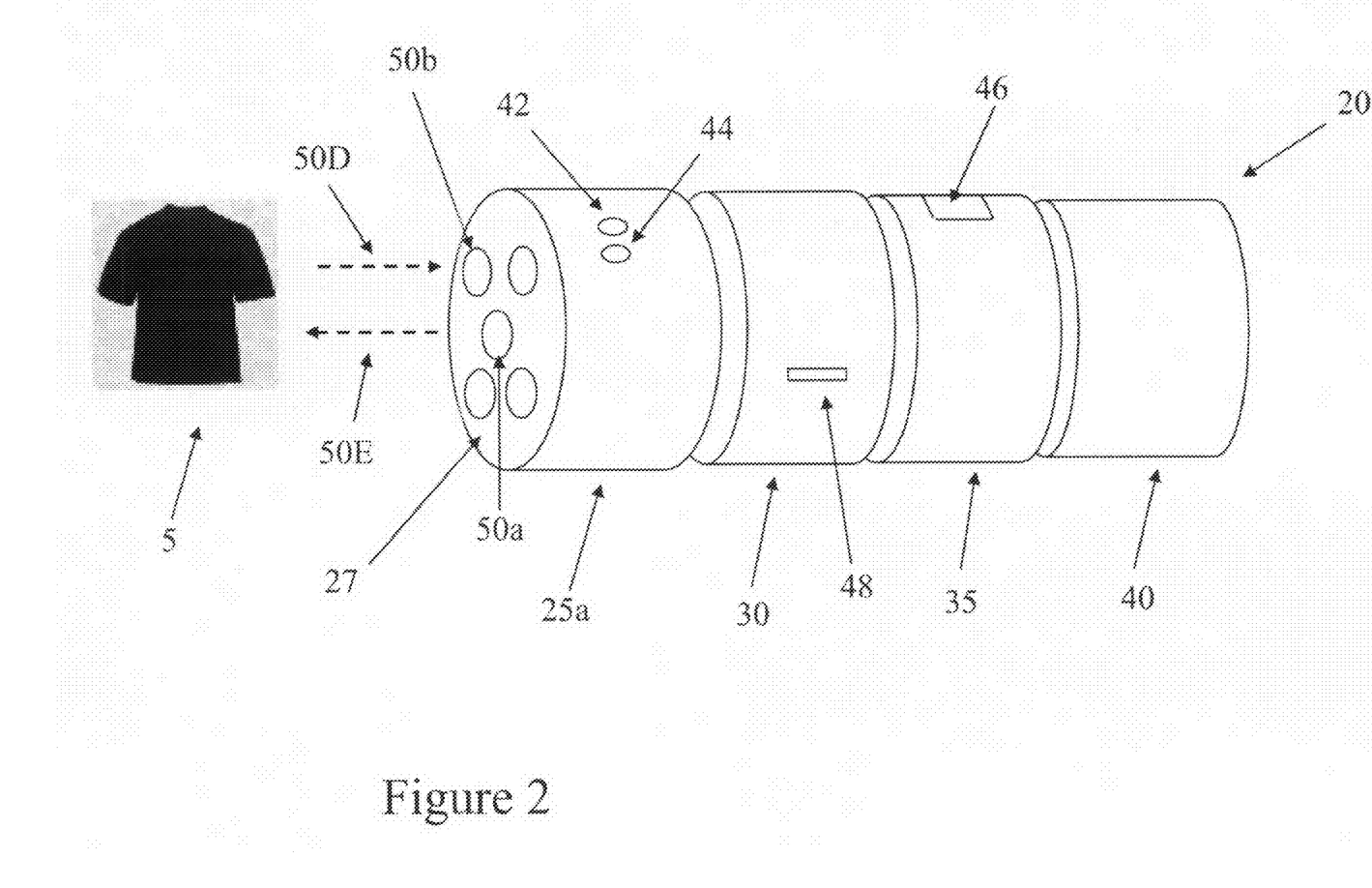
FIG. 2 illustrates a modular detection device in accordance with a first embodiment of the present invention.

Further to the preferred embodiment, FIG. 2 illustrates a modular detection device 20 including four modular components 25a, 30, 35 and 40 combined to form a hand-held detection device. More particularly, head unit module 25a includes a bank or gang of light emitting diodes (LEDs) 50a and 50b manufactured and configured, i.e., tuned, to emit 50E and detect 50D light in specific wavebands and to induce and detect fluorescence in a specific substance. As shown in FIG. 2, representative emission LED 50a is associated with representative emission path, E (50E) and representative detection LED 50b is associated with representative detection path, D (50D). The set of tuned illumination and detection LED wavebands are unique to a particular substance of interest. The head unit module 25a would be able to be detached from the rest of the modular detection device 20 and different head units could be attached where each head unit would be tuned to illuminate and detect in a different set of wavebands unique for each different substance, e.g., a first head unit module would be tuned to illuminate and detect for meth, a second head unit module would be tuned to illuminate and detect for cocaine, a third head unit module would be tuned to illuminate and detect heroin, a fourth head unit module would be tuned to illuminate and detect nitrate-based explosives, etc. The illuminating LEDs 50a would produce light in a waveband known to excite fluorescence in a particular substance. The detecting LEDs 50b are reversed biased and configured to detect light in the region of the particular substance fluorescence band (offset from illumination wave band). The use of LEDs or similar devices as detectors is described by Mims in "Sun photometer with light emitting diodes as spectrally selective detectors," APPLIED OPTICS, Vol. 31, No. 33 (20 Nov. 1992) and U.S. Pat. No. 6,410,940 which are incorporated herein by reference for their teachings.

Referring to data module 30, the data module is a data collection and output interface that receives, records/stores, and transmits/downloads data detected by the head unit module 25a. In operation, when a substance of interest is detected a scan/record mode is either automatically or manually selected directing the data module 30 to record the scan or multiple scans into a flash memory. Additional data such as head unit identification and configuration (e.g., illumination waveband, detection waveband), and signal strength, may also be collected and recorded using subcomponents either within the data module 30 or other modules of the modular detection device 20. The recorded scan information could then be retrieved by/downloaded into a computer at a later time and the detector device memory then cleared and reset for the next use with the same head unit module 25a or different head unit module tuned to detect other substances. In a preferred embodiment, the information stored in data module 30 is accessible via an I/O port, e.g., USB port 48, or may be transmitted wirelessly via, e.g., infrared ("IR") or radio frequency ("RF") transmission, to a wireless receiver.

Data from the data module can be combined in a computer file with data from other data devices such as geographic (e.g., Global Positioning System Coordinates "GPS") coordinates of the scan, photographic images of scanned surfaces and individuals, and time stamp information recording the time the scan and images were collected for later use, e.g., as potential court evidence. The modular detection device 20 may also include a camera in the head unit module 25a to record pictures, and GPS components and clock in the control module 35. The camera images and geo-location and time data would also be stored in the device's flash memory for later retrieval.

Referring to controller module 35, the controller module includes electro-mechanical subcomponents and related circuitry for supporting the operation of the modular detection device 20 including, power on/off switch 46 which may be a slider switch, push button, or other trigger, mode switches (see FIG. 3a; selector switch 60), power/charge indicator, and substance detection alert, e.g., red light, audible tone, vibration, etc. The preferred embodiment will include a microprocessor in the controller module to provide appropriate management functions to support the use of the device, for example, verifying power availability or battery charge state, proper connections among all modules, normal functionality of all modules, and providing the operator with a positive indication of device readiness, mode settings, and associated functionality. For example, referring to indicator lights 42 and 44, light 42 glows red when the fluorescent waveband to which LEDs 50*b* are tuned is detected and at all other times, i.e., when the fluorescent waveband is not being detected, light 44 glows green. Note that the embodiment shown regarding the relative locations of the data and controller modules is meant only to be representative of an embodiment for discussion purposes. The embodiment would be equally representative if the positions of the data and controller modules were reversed, i.e., in the embodied sequence head unit module, controller module, data module, and power module. The embodiment would also be equally representative if the power on/off switch 46 and the indicator lights 42 and 44 were located on other modules. Finally, referring to power module 40, the power module contains the power source of the modular detector system 20. Additionally, power module 40 consists of replaceable batteries or rechargeable batteries and a recharge socket (not illustrated), providing power/recharge capability as desired by the end user. The recharge socket would interface with a separate charging station (not shown).

The modularity of the design is an inherent feature of this technology approach. It applies to any embodiment of this technology and offers several unique features. The head unit module can be readily adapted or replaced if LED technology changes, or interchanged with other head unit modules if other substances must be detected. The controller module readily supports advanced embodiments that may require sequential or variable illuminations with concomitantly changed detection requirements for detection of new substances and/or detection in highly cluttered backgrounds. It could also be modified to provide information to the operator regarding device performance and response if such requirements may arise as a result of changes in legislation or the rules of evidence. The data module can readily accommodate the wide variety of data interfaces currently in use, and can be modified to accommodate any new interfaces that may arise as computer and other technologies advance. Finally, the power module readily accommodates the wide variety of power options available today, and can also be adapted to new power source technologies.

Figure 3A:
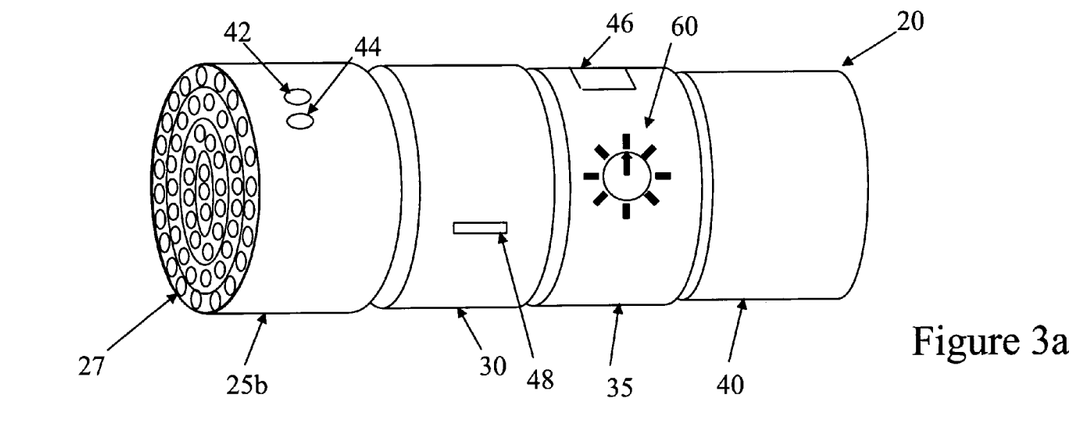
FIGS. 3a and 3b illustrate a modular detection device in accordance with a second embodiment of the present invention.
Figure 3B:
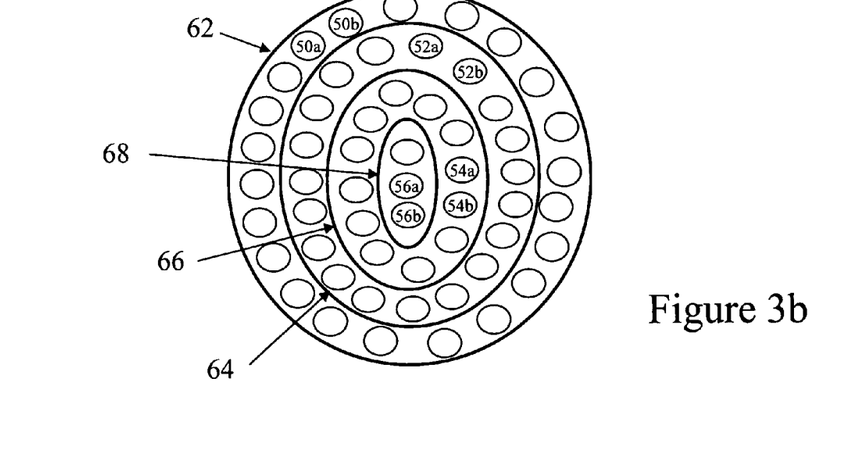

In an alternative embodiment, referring to FIGS. 3*a* and 3*b*, a single head unit module 25*b* includes a gang of LEDs 50*a*, 50*b*, 52*a*, 52*b*, 54*a*, 54*b*, 56*a*, 56*b* which illuminate and detect over a wide range of wavebands. A selector/mode switch 60 located on the controller module 35 is used to select the subset of LEDs tuned to a particular substance. Accordingly, a user is able to detect a variety of substances without having to change the head unit. In a particular exemplary configuration, each ring 62, 64, 66 and 68 of LEDs is a subset and is tuned to a particular substance of interest, e.g., ring 62 and LEDs 50*a*, 50*b* illuminate and detect meth; ring 64 and LEDs 52*a*, 52*b* illuminate and detect cocaine; ring 66 and LEDs 54*a*, 54*b* illuminate and detect heroin; ring 68 and LEDs 56*a*, 56*b* illuminate and detect marijuana. In more advanced embodiments, other substances that may be detectable by appropriate application of the technology include other illegal substances or drugs such as LSD, precursors (recipe substances) for illegal drugs, traces of nitrate-based explosives, chemical warfare agents, or toxic industrial chemicals. This is but one example of a single head unit module 25*b* configuration. Those skilled in the art can appreciate that the placement of the LEDs within the single head unit module 25*b* is limited only by the area/volume constraints of the head unit module 25*b*, by the mechanical and electrical capabilities of the controller module 35, and by the power capabilities of the power module. In addition, in an advanced embodiment, the technology herein may also be applied to the detection of various biological agents or poisons by manually or automatically sequencing the appropriate illuminating and detecting wavebands and sequentially evaluating the changes in the fluorescent responses stimulated by those illuminations to determine whether or not a particular substance or biological agent is present.

Figure 4A:
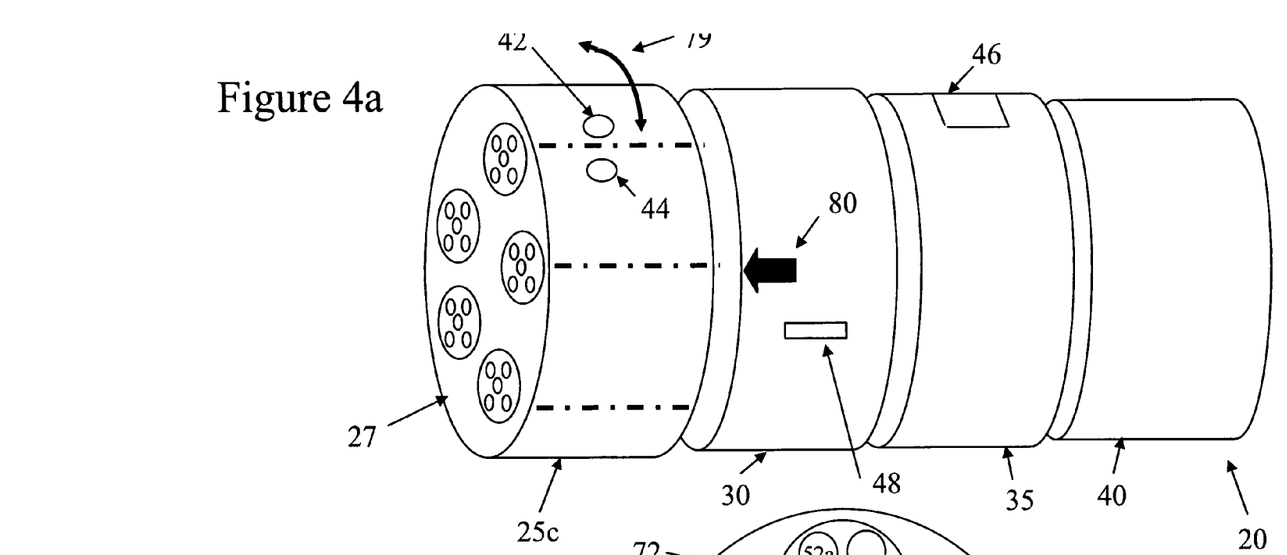
FIGS. 4a and 4b illustrate a modular detection device in accordance with a third embodiment of the present invention.
Figure 4B:
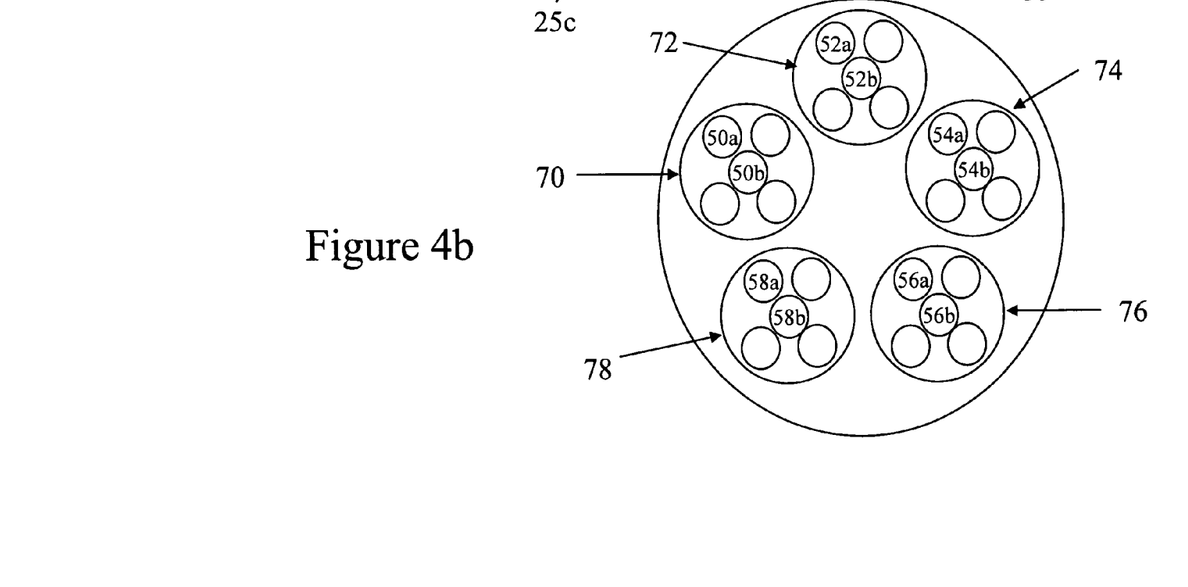

In still a further alternative embodiment, FIGS. 4*a* and 4*b* illustrate a single head unit module 25*c* wherein subsets 70, 72, 74, 76 and 78 of LED illumination and detector banks 50*a*, 50*b*; 52*a*, 52*b*; 54*a*, 54*b*; 56*a*, 56*b*; 58*a*, 58*b* are located within the single head unit module 25*c* and are selectable by rotating the head unit 25*c* as shown by bi-directional arrow 79 until the preferred subset is aligned with the arrow 80. In operation, when the power is ON, only the subset aligned with arrow 80 will emit and detect in the substance tuned wavebands. As with the embodiment exemplified above with reference to FIG. 3*a* and FIG. 3*b*, this embodiment also allows the user to utilize a single head unit module 25*b* or 25*c* to look for multiple substances.

The embodiments described herein contemplate various configurations of the emitting and detecting LEDs both alone and in relation to one another. For example, the sizes of the LEDs may not be uniform, e.g., the emitting LEDs may be smaller than the detection LEDs in order fit the requisite number of LEDs into the head unit module 25*a* or 25*b* or 25*c*. Further, the ratio of emitting LEDs to detection LEDs is not necessarily 1:1, but instead the ratio is tailored to minimize necessary power levels and maximize detection at the desired distance, e.g. approximately 4-24 inches, between the face 27 and the target 5. The ranges and exact values of the ratios, M/N, of emitting LEDs (M) to detection LEDs (N) will be determined by a combination of factors involving the specifics of the illuminating and detecting wavebands, the quantum efficiencies of the associated fluorescence phenomena, the subsequent responses of various substances to the illumination, and the nature of the various types of relevant interferent substances and clutter.

Figure 5A:
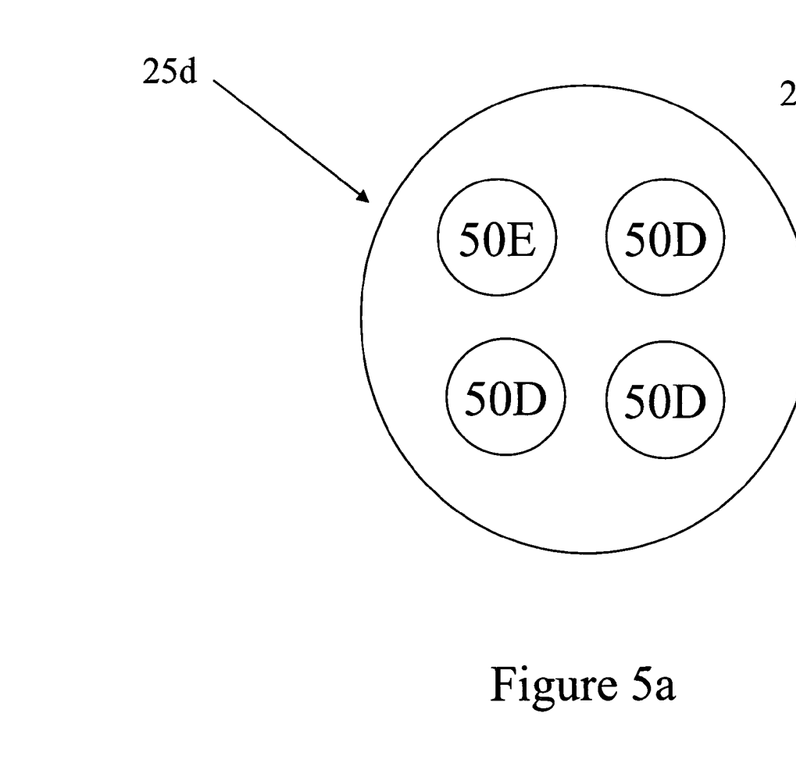
FIGS. 5a and 5b illustrate an illumination and detection module according to an embodiment of the present invention.
Figure 5B:
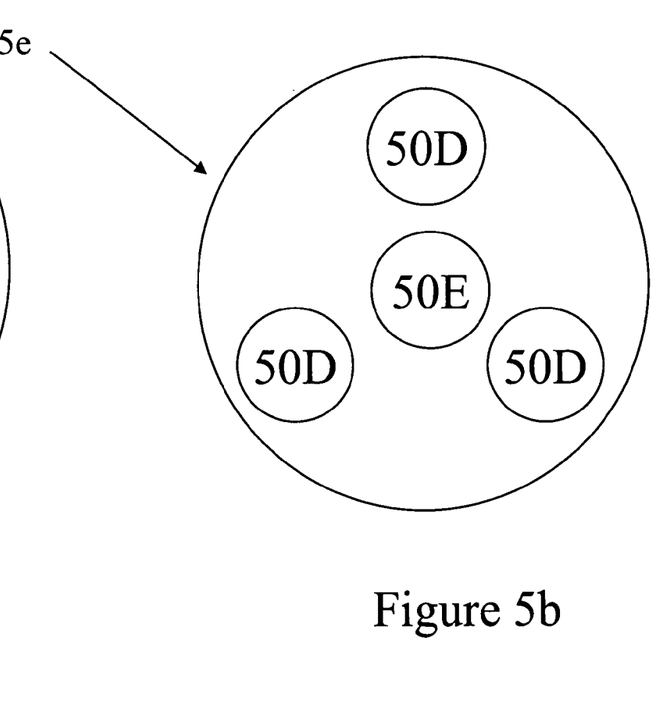
Figure 6:
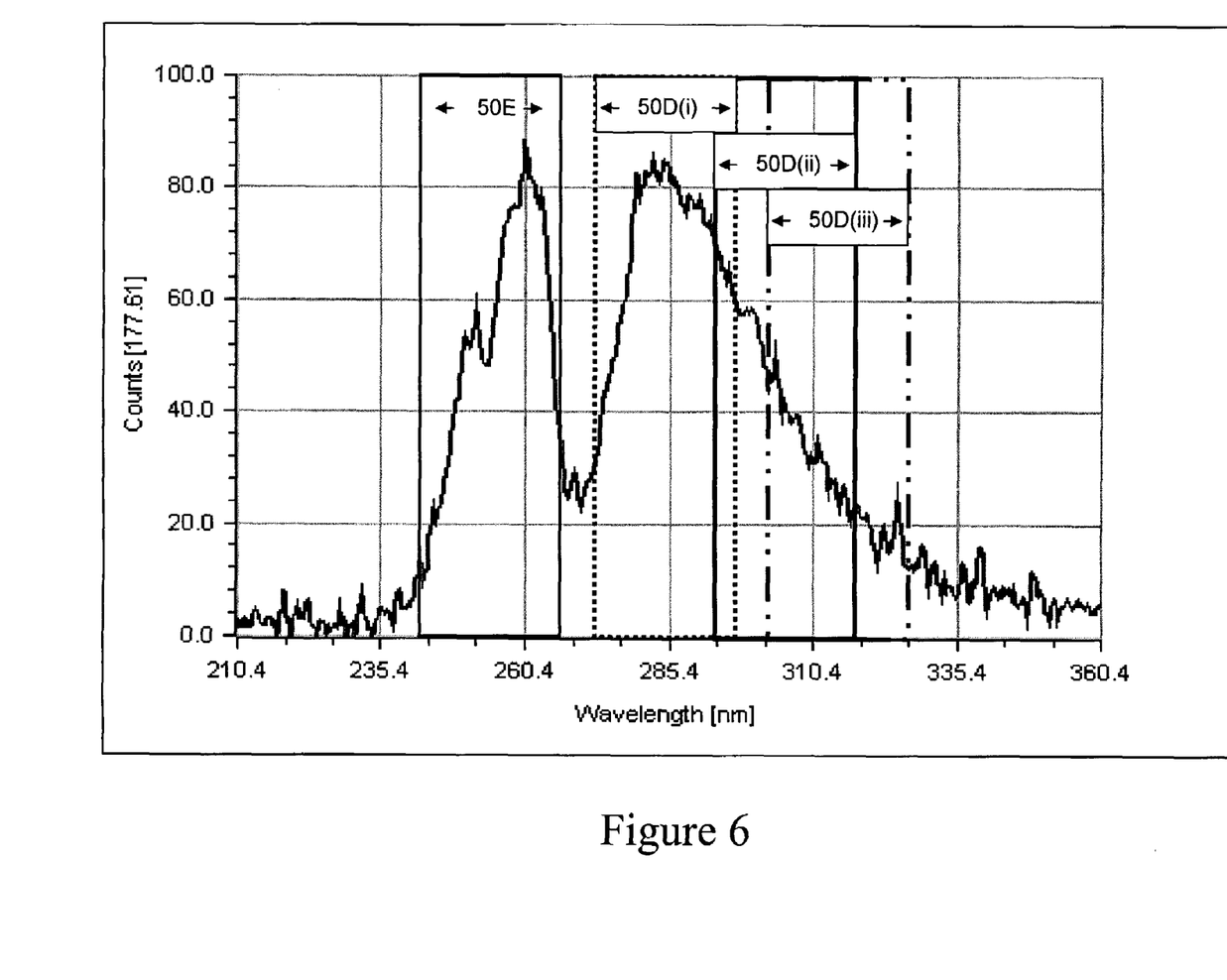
FIG. 6 illustrates LED illumination and detection sensitivity ranges overlaid on the response spectra according to an embodiment of the present invention.

For example, as shown in the head unit module embodiments 25*d* and 25*e* of FIGS. 5*a* and 5*b*, detection of methamphetamine may require only one (1) illuminating LED 50E centered at 255 nanometers, and three (3) LEDs in the detection mode 50D at wavebands centered approximately at 285, 305, and 315 nm. This may be considered an initial minimal embodiment with a ratio of 1:3. Configurations of LEDs in the head unit may be asymmetrical FIG. 5*a* or symmetrical FIG. 5*b* depending on the ratio M/N. FIG. 6 shows a spectral curve (FIG. 6 shows the same spectral curve as depicted in FIG. 1(*b*) but on an expanded scale) for this exemplary methamphetamine embodiment, wherein each of the 4 LEDs, 1 illumination 50E and 3 detection LEDs 50D(i)-50D(iii), each cover an approximately 25 nanometer range of the waveband. More particularly, in this particular example, LED 50E covers the 25 nm range centered at 255 nm; LED 50(D)(i) covers the 25 nm range centered at 285 nm; LED 50(D)(ii) covers the 25 nm range centered at 305 nm; and LED 50(D)(iii) covers the 25 nm range centered at 315 nm. For other substances and circumstances, the number of illuminator LEDs, (M) required in a particular embodiment may be greater than one (1) for at least two (2) reasons. First, more than one LED may be required to provide sufficient illumination to stimulate a more readily detectable fluorescent response. Second, more than one waveband of illumination may be needed to stimulate different responses so that substances can be identified in the presence of clutter or interferent substances.

Additionally, LED illumination and detection characteristics may vary depending on manufacturing process and/or technical advance. This may result in the need to vary the number of illuminators and detectors for each embodiment discussed within the document.

Similarly, the number (N) of detector LEDs required for detection may vary as well. For example, some substances may respond to a particular illumination waveband with a narrow-band peak at a specific characteristic wavelength that is either well-removed in wavelength from competing clutter, or has sufficient response amplitude to clearly stand well out of the clutter at nearby wavebands, i.e., exhibits a large signal-to-noise ratio. On the other hand, other substances may not have such readily detectable responses. In such cases, an embodiment using multiple LEDs at different wavebands may be needed to detect either broader or lower amplitude spectral responses with the ratios of those responses at different detection wavebands providing the basis for detection (as is the case in the initial embodiment for methamphetamine that uses three detectors to cover the response waveband). Alternatively, a substance may exhibit a series of specific, lower amplitude peaks that permit detection of the substance even in the presence of clutter. Finally, in some more advanced embodiments, it may be necessary to have both multiple illuminators and multiple detectors, as well as a stepped sequence of illumination and detection to verify the presence of the substance of interest. Those familiar with the art would recognize such configurations as being representative of a substantially advanced embodiment of the technology.

Calibration

In still a further embodiment of the present invention, a calibration subcomponent (not shown) is integrated into the charging station or built as a separate calibration module. The calibration subcomponent would be used to verify and validate modular detection device 20 operation and performance, and calibrate each tuned head module 25a or tuned subset of LEDs, e.g., subsets 62, 64, 66 and 68 of FIGS. 3a and 3b on a single head unit module 25b; subsets 70, 72, 74, 76 and 78 of FIGS. 4a and 4b on single head unit module 25c, for detection of intended target substance. The calibration for each substance would consist of an LED bank that would emit light in the target substance's fluorescence band with a rheostat to control intensity of simulated fluorescence response. The detection device would be used to scan the calibration module and detect simulated substance fluorescence. A calibration module is designed and tuned to each different substance fluorescence response. The calibration module may calibrate for a single substance or, with a gang of LEDs and selector switch to select appropriate subsets of LEDs, calibrate for multiple substances.

Operation

In a primary mode of operation, the user either secures the desired tuned head unit module 25a or selects the desired combination of LEDs on the single head module 25b or 25c with selector switch 60 or proper rotation 79, and directs the face 27 of the modular detection device 20 towards a target 5 which is being inspected for a particular substance. Targets may include clothing, body parts, trunk lids, door handles, steering wheels and interior or exterior surfaces on automobiles, and other surfaces (such as door knobs, furniture and appliance surfaces, walls, floors, ceilings, etc.) that may contain traces of a suspected substance. Referring to FIG. 2, when the power is ON, LEDs 50a, are transmitting or emitting an illumination waveband 50E and LEDs 50b are reverse biased to detect any emitted wavebands in the tuned range 50D. One skilled in the art understands how this mode of operation translates to the alternative structural embodiments described above. As an optional additional step, the user may calibrate the selected configuration utilizing the calibration subcomponent or module described above. In a preferred embodiment of the present invention, the data module 30 automatically records head unit identification/operation information, power level, time and geo-coordinates when the modular detection device 20 is powered ON. Alternatively, the modular detection device 20 may be configured such that it is necessary to manually select a validation mode. Similarly, the modular detection device 20 may require manual selection of varying modes of operation, including calibration, validation, scanning, recordation, etc. These modes may be selectable using any type of switch known to those skilled in the art.

The exemplary devices and methods described herein are capable of detecting trace amounts of the targeted substance. While what constitutes a trace amount varies depending on the substance, in general, it is expected the embodiments described herein will detect amounts down to levels at or below micrograms per square centimeter. The current art and methods used to detect various substances generally do not report their sensitivities in terms of contamination per unit area. Rather, those sensitivities are specified in terms of the absolute mass that can be detected by those methods, reported as, for example, the minimum mass required for detection on a specially prepared and packaged swab dragged across a surface, which swab is then analyzed by mass spectroscopy, gas chromatography, or other analytic methods in a laboratory or special test kit. (Guide for the Selection of Drug Detectors for Law Enforcement Applications, NIJ Guide 601-00, 1999.) Information obtained from law enforcement authorities reveals that expected levels of methamphetamine or other contaminations may be as high as milligrams per square centimeter.

The device is not limited to the tuned wavebands and substances exemplified above. The device may be used for detection of any substance with an excitable and identifiable fluorescence signature, e.g., explosives residue, hazardous chemicals such as the persistent chemical agents VX or mustard, toxic industrial chemicals such as PCBs, biological materials such as the infectious agent, anthrax, or biological poisons such as ricin. Other modular device head unit embodiments would be tuned to each different substance desired for detection.

The key features of this technology that lend themselves to these broadly scoped advanced embodiments are the monochromatic nature of the light produced by LEDs (typically, a full width at half max of 25 nanometers), the comparable narrow receptor bandwidth when operated as a detector, short response times of the LEDs in either the illumination or detection modes, the small size and weight, and the ruggedness of the LEDs themselves, the low power requirements, and the fact that the embodiment of this technology does not require the use of sensitive, precisely aligned mechanical optical paths and components. The advanced embodiment would use illuminating LEDs selected to produce specific fluorescent responses from a particular substance of interest as well as from the confounding substances likely to be present with the substance (such as precursors or recipe substances for 'cooking' meth). In addition, at any waveband, the strength of the illumination produced by an LED can be easily controlled. This two-dimensional advanced embodiment of the technology is unique to this technology, and can support rapid identification of substances of interest even in the presence of complex interferent and clutter backgrounds. In such an advanced embodiment, control of such advanced scan and detection modes, to include on-the-spot, effectively real-time analysis and diagnosis of the responses can be readily accomplished through the microchip incorporated into the control module of the device.

The device and method for use described herein are useful to numerous industries and agencies including, but not limited to, Law Enforcement (State/County/City Police), Drug Enforcement Agency, Emergency Responders (Fire, Medical, Hazmat, etc.), Healthcare (Hospitals, Medical Treatment Facilities, Doctor's Offices), Department of Transportation, Transportation Safety Agency, Alcohol Tobacco and Firearms, School Systems security (Public, Private, Universities), Environmental Protection Agency, Hazardous cleanup companies, Hotel Security, Sports Arena Security, Nightclub Security, Prison Administrators (Federal, State, City, County, Private), Veterans Association (and other halfway house authorities), Industrial facilities (Paper mills, cement companies), Trucking companies, Insurance agencies, Vehicle and Cargo Inspection, and the like. The embodiments described herein are useful to the agriculture industries for the detection of plant and forest diseases. And the invention may be useful for the following applications: screening suspects who have been apprehended including searching their person, their vehicle, and packages or other belongings in their possession; searching a room, building, car, airplane, boat, or other structure or vehicle that is suspected of storing drugs or explosives; screening prisoners in or visitors to a correctional facility as they pass through designated checkpoints; screening large numbers of people from the general public, for example, at a customs checkpoint, an airport, or at a border crossing; screening hand-carried items at busy personnel checkpoints, for example, hand-carried luggage in an airport; screening large numbers of vehicles at checkpoints such as border crossings and entrances to secure government or private facilities; screening letters, packages, and other items that pass through a mailroom, e.g., as part of a Postal services package interdiction program; screening surfaces to ensure hazardous cleanup was affective. Parents of children may use the device for monitoring possible substance related activities of the children. Additionally, the invention may be useful for detecting counterfeit products where known products are seeded with a known fluorescent marker that could be detected for validity of product, with counterfeit products detectable through absence of marker.

What is claimed is:

1. A device for determining the presence or absence of a substance comprising:
   a head unit module comprising:
      at least one illumination component configured to illuminate a target with a first waveband; and
      at least two detection components,
         wherein a first detection component is configured to detect a second waveband emitted by the target in response to the first waveband if the target contains the substance,
         wherein a second detection component is configured to detect a third waveband emitted by the target in response to the first waveband if the target contains the substance, and
         wherein each detection component is configured to detect for the presence or absence of a substance,
   wherein the head unit module comprises a plurality of subsets of illumination and detection components,
   the controller module including a subset selection component configured to facilitate the selection of a particular subset of illumination and detection components depending on a substance of interest.

2. The device according to claim 1, further comprising:
   a controller module configured to control the illumination component and the at least one detection component.

3. The device according to claim 2, further comprising:
   a power module configured to provide power to the device.

4. The device according to claim 3, further comprising:
   a data module configured to record data indicative of the presence or absence of the substance.

5. The device according to claim 1 the illumination component including at least one forward bias light emitting diode.

6. The device according to claim 5, the at least one detection component including at least one reverse-biased light emitting diode.

7. The device according to claim 6, wherein the ratio of forward bias light emitting diodes (M) and reverse bias light emitting diodes (N) is M:N.

8. The device according to claim 7, wherein the ratio M:N is 1:3.

9. The device according to claim 1, the first waveband is approximately centered at 255 nm.

10. The device according to claim 1, the second waveband is centered at approximately 285 nm.

11. The device according to claim 1, wherein the third waveband is centered at approximately 305 nm.

12. The device according to claim 1, the substance is methamphetamine.

13. The device according to claim 1, wherein each detection component is configured to detect an amount of the substance on the order of micrograms.

14. The device according to claim 1, wherein the device is handheld.

15. A device for determining the presence or absence of a substance comprising:
   a head unit module comprising:
      at least one illumination component configured to illuminate a target with a first waveband; and
      at least two detection components,
         wherein a first detection component is configured to detect a second waveband emitted by the target in response to the first waveband if the target contains the substance,
         wherein a second detection component is configured to detect a third waveband emitted by the target in response to the first waveband if the target contains the substance, and
         wherein each detection component is configured to detect for the presence or absence of a substance,
   wherein the head unit module comprises a plurality of subsets of illumination and detection components,
   the head unit module being rotatable such that a user selects a subset of illumination and detection components by rotating the single head unit and aligning a desired subset of illumination and detection components with an alignment indicator.

16. The device according to claim 15, further comprising:
   a controller module configured to control the illumination component and the at least one detection component.

17. The device according to claim 16, further comprising:
   a power module configured to provide power to the device.

18. The device according to claim 17, further comprising:
   a data module configured to record data indicative of the presence or absence of the substance.

19. The device according to claim 16, the first waveband is approximately centered at 255 nm.

20. The device according to claim 15, the illumination component including at least one forward bias light emitting diode.

21. The device according to claim 20, the at least one detection component including at least one reverse-biased light emitting diode.

22. The device according to claim 21, wherein the ratio of forward bias light emitting diodes (M) and reverse bias light emitting diodes (N) is M:N.

23. The device according to claim 22, wherein the ratio M:N is 1:3.

24. The device according to claim 15, the second waveband is centered at approximately 285 nm.

25. The device according to claim 15, wherein the third waveband is centered at approximately 305 nm.

26. The device according to claim 15, the substance is methamphetamine.

27. The device according to claim 15, wherein each detection component is configured to detect an amount of the substance on the order of micrograms.

28. The device according to claim 15, wherein the device is handheld.

29. A device for determining the presence or absence of a substance comprising:
a head unit module comprising:
at least one illumination component configured to illuminate a target with a first waveband; and
at least two detection components,
wherein a first detection component is configured to detect a second waveband emitted by the target in response to the first waveband if the target contains the substance,
wherein a second detection component is configured to detect a third waveband emitted by the target in response to the first waveband if the target contains the substance, and
wherein each detection component is configured to detect for the presence or absence of a substance,
including a calibration module containing light emitting diodes tuned to simulate a fluorescence response of the at least one substance.

30. The device according to claim 29, wherein the device is handheld.

31. The device according to claim 29, further comprising:
a controller module configured to control the illumination component and the at least one detection component.

32. The device according to claim 31, further comprising:
a power module configured to provide power to the device.

33. The device according to claim 32, further comprising:
a data module configured to record data indicative of the presence or absence of the substance.

34. The device according to claim 31, the first waveband is approximately centered at 255 nm.

35. The device according to claim 29, the illumination component including at least one forward bias light emitting diode.

36. The device according to claim 35, the at least one detection component including at least one reverse-biased light emitting diode.

37. The device according to claim 36, wherein the ratio of forward bias light emitting diodes (M) and reverse bias light emitting diodes (N) is M:N.

38. The device according to claim 37, wherein the ratio M:N is 1:3.

39. The device according to claim 29, the second waveband is centered at approximately 285 nm.

40. The device according to claim 29, wherein the third waveband is centered at approximately 305 nm.

41. The device according to claim 29, the substance is methamphetamine.

42. The device according to claim 29, wherein each detection component is configured to detect an amount of the substance on the order of micrograms.

43. A device for determining the presence or absence of a substance comprising:
a head unit module comprising:
an illumination component configured to illuminate a target with a first waveband; and
a detection component configured to detect a second waveband emitted by the target in response to the first waveband if the target contains the substance, and configured to detect a third waveband emitted by a target in response to the first waveband if the target contains the substance;
wherein the head unit module is removable from the device and replaceable with one of multiple secondary head unit modules, each secondary head unit module being configured to determine the presence or absence of a different substance.

44. The device according to claim 43, further comprising:
a controller module configured to control the illumination component and detection component.

45. The device according to claim 43, further comprising:
a power module configured to provide power to the device.

46. The device according to claim 43, further comprising:
a data module configured to record data indicative of the presence or absence of the substance.

47. The device according to claim 43, the illumination component including at least one forward bias light emitting diode.

48. The device according to claim 47, the detection component including at least one reverse-biased light emitting diode.

49. The device according to claim 48, wherein the ratio of forward bias light emitting diodes (M) and reverse bias light emitting diodes (N) is M:N.

50. The device according to claim 49, wherein the ratio M:N is 1:3.

51. The device according to claim 43, the first waveband is approximately centered at 255 nm.

52. The device according to claim 43, the second waveband is centered at approximately 285 nm.

53. The device according to claim 43, the third waveband is centered at approximately 305 mm.

54. The device according to claim 43, the substance is methamphetamine.

55. The device according to claim 43, including a calibration module containing light emitting diodes tuned to simulate a fluorescence response of the substance.

56. The device according to claim 43, wherein the detection component is configured to detect an amount of the substance on the order of micrograms.

57. The device according to claim 43, wherein the device is handheld.

* * * * *